US00PP31364P2

(12) United States Plant Patent
Jan Gerrit ten Duis

(10) Patent No.: US PP31,364 P2
(45) Date of Patent: Jan. 14, 2020

(54) ***AGASTACHE* PLANT NAMED 'CRAZY FORTUNE'**

(50) Latin Name: ***Agastache* hybrid**
Varietal Denomination: Crazy Fortune

(71) Applicant: Arend Jan Gerrit ten Duis, Haulerwijk (NL)

(72) Inventor: Arend Jan Gerrit ten Duis, Haulerwijk (NL)

( * ) Notice: Subject to any disclaimer, the term of this patent is extended or adjusted under 35 U.S.C. 154(b) by 0 days.

(21) Appl. No.: 16/350,961

(22) Filed: Feb. 4, 2019

(51) Int. Cl.
*A01H 5/02* (2018.01)

(52) U.S. Cl.
USPC ..... Plt./399

(58) Field of Classification Search
USPC ..... Plt./399
CPC ..... A01H 5/02
See application file for complete search history.

*Primary Examiner* — Annette H Para
(74) *Attorney, Agent, or Firm* — Penny J. Aguirre

(57) ABSTRACT

A new cultivar of *Agastache* plant named 'Crazy Fortune' that is characterized by its lowers that are blue-purple in color, its mature leaf variegation that is white and green in color, and its foliage that is dark green in color, its compact and well branched plant habit, its good winter hardiness, and its young leaf variegation that is purple, white and green in color.

2 Drawing Sheets

Botanical classification: *Agastache* hybrid
Variety denomination: 'Crazy Fortune'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

BACKGROUND OF THE INVENTION

The present invention relates to a new and distinct cultivar of *Agastache* hybrid and will be referred to hereafter by its cultivar name, 'Crazy Fortune'. 'Crazy Fortune' is an herbaceous perennial grown for landscape use.

The Inventor discovered the new cultivar in summer of 2012 as a naturally occurring branch mutation of *Agastache* 'Blue Fortune' (not patented) in a field block at his nursery in Haulerwijk, The Netherlands.

Asexual propagation of the new cultivar was first accomplished by the Inventor by stem cuttings in 2016 in Haulerwijk, The Netherlands. Asexual propagation of the new cultivar by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Crazy Fortune' as a unique cultivar of *Agastache*.

1. 'Crazy Fortune' exhibits flowers that are blue-purple in color.

2. 'Crazy Fortune' exhibits mature leaf variegation that is white and green in color.
3. 'Crazy Fortune' exhibits young leaf variegation that is purple, white and green in color.

'Blue Fortune', the parent plant of 'Crazy Fortune', is similar to 'Crazy Fortune' in flower color and plant size. 'Blue Fortune' differs from 'Crazy Fortune' in having leaves that lack variegation. 'Crazy Fortune' can be compared to typical plants of *Agastache foeniculum*, which are similar in having blue-purple flowers, but differ in lacking variegated foliage and in having much smaller inflorescences.

BRIEF DESCRIPTION OF THE DRAWINGS

The accompanying colored photographs illustrate the overall appearance and distinct characteristics of a 1-year-old plant of the new *Agastache* as grown in a 2-liter container in Haulerwijk, The Netherlands.

The photograph in FIG. 1 provides a side view of 'Crazy Fortune' in bloom.

Figure 1:
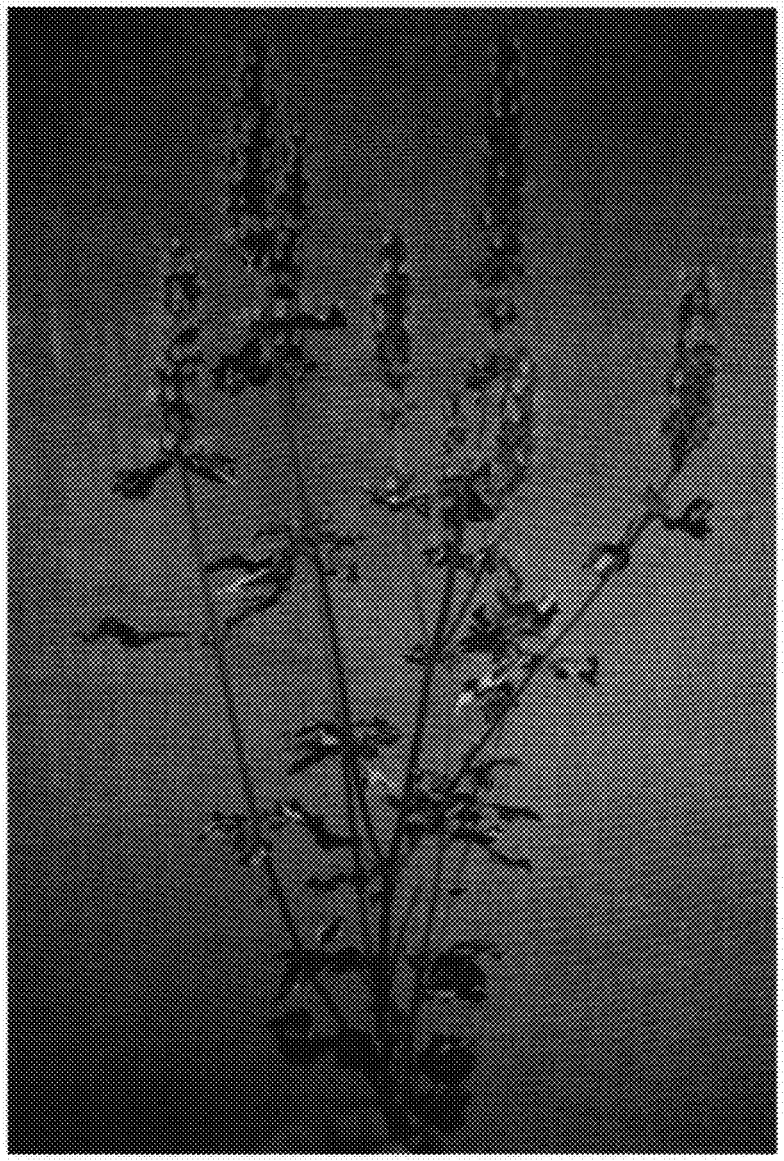
Figure 2:
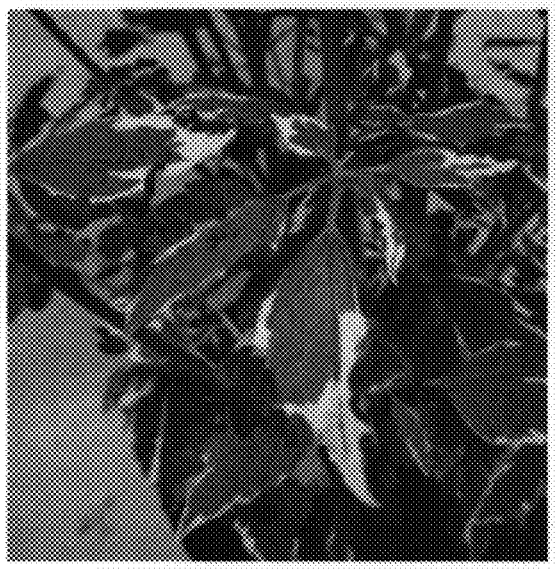

The photograph in FIG. 2 provides a close-up view of a mature inflorescence of 'Crazy Fortune'.

Figure 3:
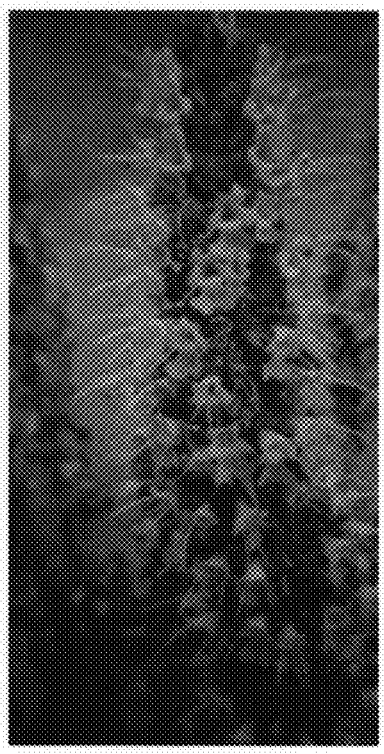

The photograph in FIG. 3 provides a close-up view of an emerging inflorescence and the young foliage of 'Crazy Fortune'.

Figure 4:
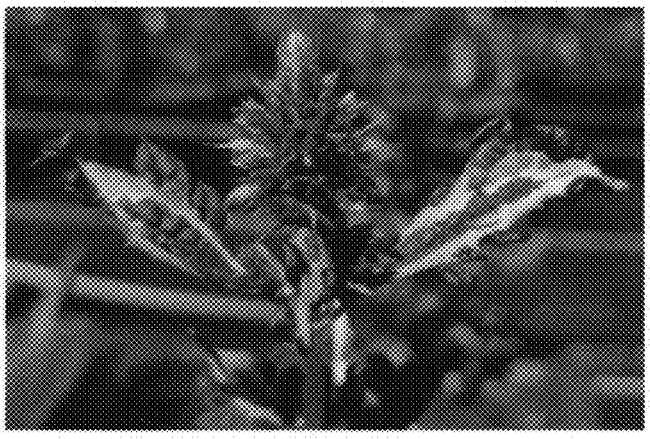

The photograph in FIG. 4 provides a close-up view of the mature foliage of 'Crazy Fortune'.

The colors in the photographs may differ slightly from the color values cited in the detailed botanical description, which accurately describe the colors of the new *Agastache*.

DETAILED BOTANICAL DESCRIPTION

The following is a detailed description of the new cultivar of plants 1-year-old in age as grown outdoors in 2-liter containers in Haulerwijk, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—July to September in The Netherlands.

*Plant type.*—Herbaceous perennial.

*Plant shape.*—Oblanceolate.

*Plant habit.*—Upright.

*Plant size.*—Average of 45 cm in height (excluding inflorescence), 70 cm in height (including inflorescence) and 50 cm in diameter as a mature plant in the landscape.

*Cold hardiness.*—At least in U.S.D.A. Zones 7 to 11.

*Diseases and pests.*—No susceptibility or resistance to diseases or pests has been observed.

*Root description.*—Fibrous, 161C.

*Root development.*—Roots develop in a P14 container in about 8 weeks.

*Propagation.*—Stem cuttings.

*Growth rate.*—Moderate to high.

Stem description:

*Shape.*—Quadrangular.

*Stem color.*—Young stems; 144C, mature stems; 144A.

*Stem size.*—Up to 70 cm in length including the inflorescence, 5 mm in diameter.

*Stem surface.*—Dull and very sparsely covered with very short hairs, slightly more densely so at the nodes.

*Stem aspect.*—Main branches 90° , lateral branches 70° to 80° from horizontal.

*Internode length.*—Ranges between 1.5 cm and 10 cm.

*Branching.*—Branches from the base, average of 12 primary branches and 8 lateral branches.

*Stem strength.*—Strong.

Foliage description:

*Leaf shape.*—Ovate to lanceolate.

*Leaf division.*—Simple.

*Leaf base.*—Cuneate to oblique.

*Leaf apex.*—Ranges from acute to acuminate to apiculate.

*Leaf venation.*—Pinnate, upper surface color; 143C, lower surface color; 138D.

*Leaf margins.*—Coarsely serrated and irregularly with one wave.

*Leaf arrangement.*—Opposite.

*Leaf attachment.*—Petiolate.

*Leaf surface.*—Both surfaces are slightly rugose, matte, and glabrous.

*Leaf variegation.*—Mainly between the middle of the leaf and the margin, band-like, sometimes touching the margin, sometimes also in the middle but then mainly towards the apex.

*Leaf size.*—Average of 7 cm in length and 4 cm in width.

*Leaf color.*—Young upper surface; main color 139A and variegated with 155A, 138B, and N80B, young lower surface; main color 138B and variegated with 155A, 138B, and N80B, mature upper surface; main color 139A, and variegated with 155A and 139C, and 138B, mature lower surface; 138B and variegated with 155A and 139C.

*Fragrance.*—Slightly sweet minty fragrance.

*Petioles.*—Ranges between 6 mm and 1.8 cm in length and 1.2 mm in diameter, upper surface matte, sparsely covered with very short hairs, lower surface glabrous, upper surface matte, 143C in color, lower surface 144A in color, strong strength.

Inflorescence description:

*Inflorescence type.*—Raceme (spike) with opposite dichasial cyme, lower cyme pairs with gaps.

*Lastingness of inflorescence.*—Individual flowers average of 2 days, self cleaning.

*Inflorescence size.*—3 cm to 20 cm in height and 2 cm in diameter.

*Flower type.*—Labiate.

*Flower aspect.*—Outward.

*Flower number.*—Average of 200 to 300 per inflorescence.

*Flower shape.*—Small oblong, labiate.

*Flower rachis (peduncle).*—3 to 20 cm in length, 1.3 mm to 2.5 mm in diameter, 144A in color, covered with short pubescence, longevity average of 3 to 5 weeks.

*Raceme bract.*—Average of 1, average of 4 cm in length, 3 mm in width, ovate to oblanceolate in shape, acuminate apex, cuneate base, entire margins, upper and lower surface color 137D and NN155B and heavily suffused with N89D on immature flowers, upper and lower surface sparsely covered with pubescent hairs.

*Flower fragrance.*—None.

*Flower buds.*—Obovate in shape, 4.5 mm in length, 1.5 mm in diameter, matte surface, sparsely covered with pubescence hairs, 138C in color.

*Flower size.*—Average of 6 mm in height, 3.5 mm in diameter, 7.5 cm in length, throat diameter is 1.5 mm, tube length is 6 mm, tube 1.5 mm in diameter but 0.8 mm at the base.

*Peduncle.*—Not present, cymes sessile.

*Pedicels.*—Not present, flowers sessile.

*Calyx.*—comprised of 5 sepals, rotate, 1 whorl, fused, campanulate in shape, entire margin, acute apex, 6.5 mm in length, 4 mm in width, entire margins, upper and lower surface glabrous, when opening and fully open upper surface 138C, when opening and fully open upper and lower surface 90C with 137D at margins.

*Petals.*—5 (4 similar petals and 1 odd-shaped lower petal), fused at base, labiate, upper lip; obovate in shape, margin entire, apex subacute to obtuse, 1.3 mm in length and 1.5 mm in width, based fused, upper and lower surface smooth, matte, sparsely covered with short hairs, glabrous, color when opening and fully open upper and lower surface 92B, throat color upper and lower surface 92D, base 157D, lower lip; broadly obovate in shape, margin entire, apex strongly emarginate, 2.5 mm in length and 3.7 mm in width, base fused, color and surface matches upper petals description.

Reproductive organs:

*Gynoecium.*—Pistil; 1, 1.1 cm in length, stigma; cleft (2 parted), and 91A in color, ovary; 144C in color.

*Androcoecium.*—Stamens; 4, filaments; 4, glabrous surface, 2 mm in length, 91A, fading lighter towards the base to 91B in color, anthers; broadly oblong, 0.3 mm in length and width, N92A in color, pollen; moderate in quantity and N92A in color.

*Fruit and seed.*—None have been observed to date.

It is claimed:

1. A new and distinct cultivar of *Agastache* plant named 'Crazy Fortune' as herein illustrated and described.

* * * * *